(12) United States Patent
Bennett

(10) Patent No.: US 7,267,984 B2
(45) Date of Patent: Sep. 11, 2007

(54) RECOMBINATION ASSEMBLY OF LARGE DNA FRAGMENTS

(75) Inventor: George Nelson Bennett, Houston, TX (US)

(73) Assignee: Rice University, Houston, TX (US)

( * ) Notice: Subject to any disclaimer, the term of this patent is extended or adjusted under 35 U.S.C. 154(b) by 365 days.

(21) Appl. No.: 10/699,512

(22) Filed: Oct. 31, 2003

(65) Prior Publication Data

US 2004/0096891 A1    May 20, 2004

Related U.S. Application Data

(60) Provisional application No. 60/422,748, filed on Oct. 31, 2002.

(51) Int. Cl.
   *C12N 15/00* (2006.01)
   *C12N 15/87* (2006.01)

(52) U.S. Cl. ........................... 435/440; 435/462

(58) Field of Classification Search ............ None
   See application file for complete search history.

(56) References Cited

U.S. PATENT DOCUMENTS 5,888,732 A *  3/1999  Hartley et al. ............ 435/6
   2002/0007051 A1 *  1/2002  Cheo et al. ............. 536/23.1

FOREIGN PATENT DOCUMENTS

WO    WO 01/11058 A1 *  2/2001

OTHER PUBLICATIONS

Martinez-Morales, F., et al., Chromosomal integration of heterologous DNA in *Escherichia coli* with precise removal of markers and replicons used during construction. J Bacteriol, 1999. 181(22): p. 7143-8.

Koob, M.D., et al., Minimizing the genome of *Escherichia coli*. Motivation and strategy. Ann N Y Acad Sci, 1994. 745: p. 1-3.

Peredelchuk, M.Y. and G.N. Bennett, A method for construction of *E. coli* strains with multiple DNA insertions in the chromosome. Gene, 1997. 187(2): p. 231-8.

Lorbach, E., et al., Site-specific recombination in human cells catalyzed by phage lambda integrase mutants. J. Mol Biol, 2000. 296(5): p. 1175-81.

Cherepanov, P. P. and W. Wackernagel, Gene disruption in *Escherichia coli*: TcR and KmR cassettes with the option of Flp-catalyzed excision of the antibiotic-resistance determinant. Gene, 1995. 158(1): p. 9-14.

Chiang, S.L. and J.J. Mekalanos, Construction of a *Vibrio cholerae* vaccine candidate using transposon delivery and FLP recombinase-mediated excision. Infect Immun, 2000. 69(11): p. 6391-7.

Tsuda, M., Use of a transposon-encoded site-specific resolution system for construction of large and defined deletion mutations in bacterial chromosome. Gene, 1998. 207(1): p. 33-41.

Dale, E.C. and D.W. Ow, Gene transfer with subsequent removal of selection gene from the host genome. Proc Natl Acad Sci U S A, 1991. 88(23): p. 10558-62.

Delneri, D., et al., Exploring redundancy in the yeast genome: an improved strategy for use of the cre-loxP system. Gene, 2000. 252(1-2): p. 127-35.

Palmeros, B., et al., A family of removable cassettes designed to obtain antiobiotic- resistance-free genomic modifications of *Escherichia coli* and other bacteria. Gene, 2000. 247(1-2): p. 255-64.

Mao, X., Y. Fujiwara, and S.H. Orkin, Improved reporter strain for monitoring Cre recombinase-mediated DNA excisions in mice. Proc Natl Acad Sci U S A, 1999. 96(9): p. 5037 42.

Caparon, M.G. and J.R. Scott, Excision and insertion of the conjugative transposon Tn916 involves a novel recombination mechanism. Cell, 1989. 59(6): p. 1027-34.

Storrs, M. J., et al., Conjugative transposition of Tn916 requires the excisive and integrative activities of the transposon-encoded integrase. J Bacteriol, 1991, 173(14): p. 4347-52.

Manganelli, R., S. Ricci, and G. Pozzi, Conjugative transposon Tn916: evidence for excision with formation of 5'-protruding termini. J Bacteriol, 1996. 178(19): p. 5813-6.

Rudy, C., et al., Excision of a conjugative transposon in vitro by the Int and Xis proteins of Tn916. Nucleic Acids Res, 1997. 25(20): p. 4061-6.

Connolly, K.M., M. Iwahara, and R.T. Clubb, Xis protein binding to the left arm stimulates excision of conjugative transposon Tn916. J Bacteriol, 2002. 184(8): p. 2088-99.

Platt, R., et al., Genetic system for reversible integration of DNA constructs and lacZ gene fusions into the *Escherichia coli* chromosome. Plasmid, 2000. 43(1): p. 12-23.

(Continued)

Primary Examiner—Jeffrey Fredman
(74) Attorney, Agent, or Firm—Baker & McKenzie LLP

(57) ABSTRACT

A method of assembling large DNA fragments in a chromosome using site specific recombinases and alternating excisionases. The method may be performed in vitro or in vivo, but larger assemblies are possible when the assembly is performed in vivo. For an in vivo assembly, the cell must be engineered to contain the desired recombinases, each in an inducible construct so that the desired recombinase can be expressed at the correct time with the correct choice of inducing agent.

8 Claims, 3 Drawing Sheets

OTHER PUBLICATIONS

Kim, S.Y., et al., Modification of bacterial artificial chromosome clones using Cre recombinase: introduction of selectable markers for expression in eukaryotic cells. Genome Res, 1998. 8(4): p. 404-12.

Golic, M.M., et al., FLP-mediated DNA mobilization to specific target sites in *Drosophila chromosomes*. Nucleic Acids Res, 1997. 25(18): p. 3665-71.

Christ, N., T. Corona, and P. Droge, Site-specific recombination in eukaryotic cells mediated by mutant lambda intergrases: implications for synaptic complex formation and the reactivity of episomal DNA segments. J Mol Biol, 2002. 319(2): p. 305-14.

Call, L.M., et al. A cre-lox recombination system for the targeted integration of circular yeast artificial chromosomes into embryonic stem cells. Hum Mol Genet, 2000. 9(12): p. 1745-51.

Feng, Y.Q., et al., Site-specific chromosomal integration in mammalian cells: highly efficient CRE recombinase-mediated cassette exchange. J Mol Biol, 1999. 292(4): p. 779-85.

Thyagarajan, B., et al., Mammalian genomes contain active recombinase recognition sites. Gene, 2000. 244(1-2): p. 47-54.

Diaz, V., et al., The prokaryotic beta-recombinase catalyzes site-specific recombination in mammalian cells. J Biol Chem, 1999. 274(10): p. 6634-40.

Olivares, E.C., R.P. Hollis, and M.P. Calos, Phage R4 integrase mediates site-specific integration in human cells. Gene, 2001. 278(1-2): p. 167-76.

Moskowitz, I.P., K.A. Heichman, and R.C. Johnson, Alignment of recombination sites in Hin-mediated site-specific DNA recombination. Genes Dev, 1991. 5(9): p. 1635-45.

Haykinson, M.J., et al., The Hin dimer interface is critical for Fis-mediated activation of the catalytic steps of site-specific DNA inversion. Curr Biol, 1996. 6(2): p. 163-77.

Merickel, S.K., M.J. Haykinson, and R.C. Johnson, Communication between Hin recombinase and Fis regulatory subunits during coordinate activation of Hin-catalyzed site-specific DNA inversion. Genes Dev, 1998. 12(17): p. 2803-16.

Stark, W.M., M.R. Boocock, and D.J. Sherratt, Site-specific recombination by Tn3 resolvase. Trends Genet, 1989. 5(9): p. 304-9.

Arnold, P.H., et al., Mutants of Tn3 resolvase which do not require accessory binding sites for recombination activity. Embo J, 1999. 18(5): p. 1407-14.

Canosa, I., et al., Site-specific recombination by the beta protein from the streptococcal plasmid pSM19035: minimal recombination sequences and crossing over site. Nucleic acids res, 1996. 24(14): p. 2712-7.

Canosa, I., et al., beta Recombinase catalyzes inversion and resolution between two inversely oriented six sites on a supercoiled DNA substrate and only inversion on relaxed or linear substrates. J Biol Chem, 1998. 273(22): p. 13886-91.

Muyrers, J.P., et al., Point mutation of bacterial artificial chromosomes by ET recombination. EMBO Rep, 2000. 1(3): p. 239-43.

Muyrers, J.P., et al., Rapid modification of bacterial artificial chromosomes by ET-recombination. Nucleic Acids Res, 1999. 27(6): p. 1555-7.

Yoon, Y.G., J.H. Cho, and S.C. Kim, Cre/loxP-mediated excision and amplification of large segments of the *Esherichia coli* genome. Genet Anal, 1998. 14(3): p. 89-95.

Cheng, T.H., et al., Controlling gene expression in yeast by inducible site-specific recombination. Nucleic Acid Res, 2000. 38(24): p. E108.

Choi, S., et al., A new approach for the identification and cloning of genes: the pBACwich system using Cre/lox site-specific recombination. Nucleic acids Res, 2000. 28(7): p. E19.

Sclimenti, C.R., B. Thyagarajan, and M.P. Calos, Directed evolution of a recombinase for improved genomic integration at a native human sequence. Nucleic Acids Res, 2001. 29(24): p. 5044-51.

Johnson, R.C., Bacterial Site-Specific DNA Inversion Systems, in Mobile DNA II, N.L. Craig, Craigie, R., Gellert, M., Lambowitz. A. M., Editor. 2002, ASM Press: Washington, D.C. p. 230-271.

Grindley, N.D.F., The Movement of Tn3-Like Elements: Transposition and Cointegrate Resolution, in Mobile DNA II, N.L. Craig, Craigie, R., Gellert, M., Lambowitz. A.M., Editor. 2002. p. 272-302.

Posfai, G., et al., In vivo excision and amplification of large segments of the *Escherichia coli* genome. Nucleic Acids Res, 1994. 22(12): p. 2392-8.

Buchholz, F., P.O. Angrand, and A.F. Stewart, Improved properties of FLP recombinase evolved by cycling mutagenesis. Nat Biotechnol, 1998. 16(7): p. 657-62.

Scott, J.R., et al., Conjugative transposition of Tn916: preferred targets and evidence for conjugative transfer of a single strand and for a double-stranded circular intermediate. Mol Microbiol, 1994. 11(6): p. 1099-108.

Poyart-Salmeron, C., et al., The integration-excision system of the conjugative transposon Tn 1545 is structurally and functionally related to those of lambdoid phages. Mol Microbiol, 1990. 4(9): p. 1513-21.

Trieu-Cuot, P., et al., Sequence requirements for target activity in site-specific recombination mediated by the Int protein of transposon Tn 1545. Mol Microbiol, 1993. 8(1): p. 179-85.

Sauer, B. and N. Henderson, Targeted insertion of exogenous DNA into the eukaryotic genome by the Cre recombinase. New Biol, 1990. 2(5): p. 441-9.

Johnson, R.C., Mechanism of site-specific DNA inversion in bacteria. Curr Opin Genet Dev, 1991. 1(3): p. 404-11.

Rojo, F. and J.C. Alonso, The beta recombinase of plasmid pSM19035 binds to two adjacent sites, making different contacts at each of them. Nucleic Acids Res, 1995. 23(16): p. 3181-8.

Huang, L.C., E.A. Wood, and M.M. Cox, A bacterial model system for chromosomal targeting. Nucleic Acids Res, 1991. 19(3): p. 443-8.

* cited by examiner

Figure 2. Integration and Excision Scheme

RECOMBINATION ASSEMBLY OF LARGE DNA FRAGMENTS

PRIOR RELATED APPLICATIONS

This patent application claims priority to U.S. Provisional Application Ser. No. 60/422,748, filed on Oct. 31, 2002, the disclosure of which is incorporated by reference in its entirety herein.

FEDERALLY SPONSORED RESEARCH STATEMENT

Not applicable.

REFERENCE TO MICROFICHE APPENDIX

Not applicable.

FIELD OF THE INVENTION

A process for recombination assembly of a series of cloned DNA fragments into a large ordered arrangement.

BACKGROUND OF THE INVENTION

With the structural analysis of DNA proceeding at a rapid pace based on the advances in DNA sequencing techniques and encouraged by potential applications of information from completely sequenced genomes of important organisms, a new chemical horizon is the synthesis of large DNA structures. This endeavor follows the trend of past chemical work on molecules of all types; first, determination of the structure, then synthesis of the structure for confirmation and producing novel structures and analogs to investigate their properties. A number of DNA analogs have been synthesized for special purposes (peptide backbone DNA, DNA with modified phosphoryl groups) and special sequence segments have been designed to interact with double helical DNA. In the case of microbial genomes, there has been discussion of preparing a minimal genome. However, general methods for constructing large precisely designed DNA segments have not been developed.

Presently, commercially available oligonucleotide synthesis can routinely produce molecules on the order of a hundred nucleotides, and through PCR amplification of known segments of a genome, defined fragments of up to 40 kilobase pairs can be prepared. Through cleavage with specific restriction enzymes and joining by ligation, designed DNA molecules (e.g., large vectors) have been made. However, this method becomes complicated as larger fragments with more restriction sites are used and each molecule to be made must have its unique route of synthesis depending on its particular arrangement of restriction endonuclease sites. The protection of certain sites by specific methylases and the recent discovery of several very rare cleaving endonucleases have extended the range of manipulations available from this basic approach.

Cloning techniques have been used to isolate and propagate large fragments on special vectors (BAC, YACs) and homologous DNA recombination has allowed the reconstruction of known chromosomal regions of over a hundred kilobase pairs. Improved systems for direct recombination have made functional studies of genes easier through "gene knockout technology" [4]. However, the defined assembly of a novel DNA sequence of large size has not been carried out. In order to produce large designed segments that are composed of DNA sections not normally together (or not even from the same organism), new methodologies need to be developed.

Potential uses for these techniques are in areas such as the analysis of function of large interrupted coding regions that exist in many human genes, and in the construction of gene sets involved in complex metabolic processes [2]. These techniques could allow for more extensive genetic reprogramming of microbes for optimal production processes (metabolic engineering) and proposals for large scale "editing" of known genomes have been made based on engineering optimization considerations [3]. Methods for the generation of such DNA would allow the formation of optimized strains for industry and provides a way to explore global structural effects in the function of microbial genomes.

SUMMARY OF THE INVENTION

A general synthetic approach for the formation of designed unique DNA molecules of a size of hundreds of kilobase pairs has been developed. In general, the technique uses site specific recombinases to insert a vector containing a fragment of interest into a specific location on DNA in the cell. The chromosome or plasmid has been manipulated to contain a single recombinase site and a single excision site. These sites can be incorporated in to the cell DNA by any means known in the art, for example homologous recombination at the lac operon with the appropriate vectors.

Next, the unneccesary vector sequences are excised by a first excisionase, thus bringing the fragment of interest adjacent to a prior inserted fragment and leaving the initial site specific recombinase site intact. This is possible because the vector also contains a site specific excision site (e.g. a recombinase site in the reverse orientation to that found in the recipient DNA).

This process is repeated with a second vector that contains the same site specific recombinase site and a single excision site from a second excision enzyme. The first vector also included the second excision site in the opposite orientation. Thus, incorporation of the second vector into the chromosome now allows the intervening vector sequences to again be removed with the second excisionase.

Using alternating excisionases, an unlimited number of fragments can be aligned adjacent in the chromosome, BAC or YAC DNA. We have exemplified the method using alternating excisionases for simplicity, but of course, three or more excisionases may be used and this is explicitly stated to be an equivalent of using two excisionases. When fragment assembly is complete, a final excisionase can be used to excise and circularize the assembled fragment provided the final excisionase sites were appropriately placed in the chromosome (or DNA element in the cell) and the final vector.

The cre-lox system is the most commonly used site specific recombination system, but the art teaches a very large variety of site specific recombinases that are too numerous to name. Many of these recombinases can be employed as an "excisionase" in the context of this invention, merely by placing the sites in the opposite orientation (See FIG. 1). Suitable site specific recombinases include FRT, hix/hin, FlpR, xerD, shufflon, SSV1 integrase, and members of the Tn3 family, including the IS6 family of recombinases. Features of several site specific recombinases are mentioned below.

Several site specific recombinases have been used for excision of fragments from chromosomal DNA in *E. coli* or other organisms. Applications have included the removal of antibiotic resistance elements after a genetic manipulation. The lambda int/xis system has been used in *E. coli* [5] and mammalian cells [6]. The FRT/FLP system from yeast has been used in *E. coli* [7] [2], *Vibrio* [8], and has shown capability for deletion of large segments of 100 kb in *E. coli* [9]. A genetically improved flp recombinase has also been utilized [10]. A similar size deletion was also made in *E. coli* with the cre/lox system [11] and in *Pseudomonas* by the site-specific resolution system of Tn1722 [12].

The Cre/lox system is one of the most widely used systems for deletions in plant [13], yeast [14, 15], *E. coli* [16], and mammalian systems [17]. Another group of sie specific recombinases capable of precise deletion, or excision of the transposon are those derived from the conjugative transposons. The deletion of the transposon from insertion sites placed in *E. coli* has been studied with the transposons Tn916 and Tn1545. Analysis of the lambda int-like enzymes [18, 19], sites [20] and in vitro mechanism [21-23] of Tn 916 or Tn1545 [24, 25] has shown how these can be used to insert and excise DNA contained within the ends of the transposon.

Recombination of a plasmid bearing a site for action of a recombinase into chromosome of a host cell has been used for manipulation in *E. coli* via the lambda system [6, 26] the Flp Frt system [27], or the cre/lox system [28]. The cre lox system has been used to bring large fragments (230 kb) into plant chromosomes [29]. Site specific recombinases have been used to manipulate the chromosomes of *Drosophilia* (Flp-frt system) [30] and a concerted effort has shown the application of a number of systems in mammalian cells; lambda int system [31], phage phiC31 integrase [32], cre/lox [33, 34], [35], [36], *streptococcal* plasmid beta recombinase [37], and phage R4 integrase [38].

Another group of recombinases capable of site specific deletion reactions include some of those usually involved in inversion of segments of the genome (invertase family) or resolution of dimeric structures after replication or cointegrate formation (resolvase family). In the Hin/hix inversion system [39] [40], inversion is preferred over deletion [41]. These recombinases are stimulated by binding of Fis at a nearby site. Mutants of Hin which can catalyze deletions at high frequency have been described [42]. These mutations are in the E-helix as with Gin and other related recombinases that have lost enhancement or specificity functions.[43]

In the case of Tn3 resolvase [44] [45], a mutant resolvase, with a D102Y mutation [46] can act on inverted res sites as well as acting on a pair of sites one of which has a full res site and the other which contains only binding site I, and not binding site II or III of the full res site.

Recently the beta recombinase of pSM19035 has been studied and the minimal recognized recombination site has been defined [47], a 90 bp site with two binding site elements (site I and II) with recombination taking place in site I. [48]. Resolution also occurs on inverted sites in supercoiled plasmids [49], so an excision event can also be catalyzed.

We have exemplified the system using FRT as the site specific recombinase, hin/hix as the first excisionase, TnE (L/R)/Tn excisionase as the second excisionase, and cre-lox as the final excisionase. The method is illustrated in FIGS. 2A and 2B.

DESCRIPTION OF EMBODIMENTS OF THE INVENTION

Figure 1:
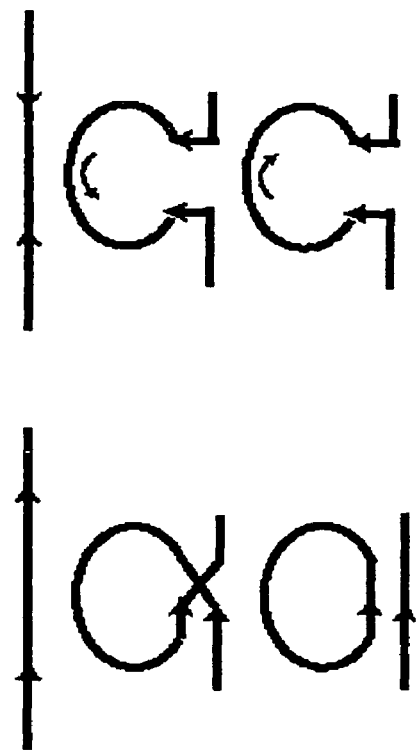
FIG. 1. Kinds of Site Specific Recombinases
FIGS. 2A and 2B. Integration and Excision Scheme.
Figure 2A:
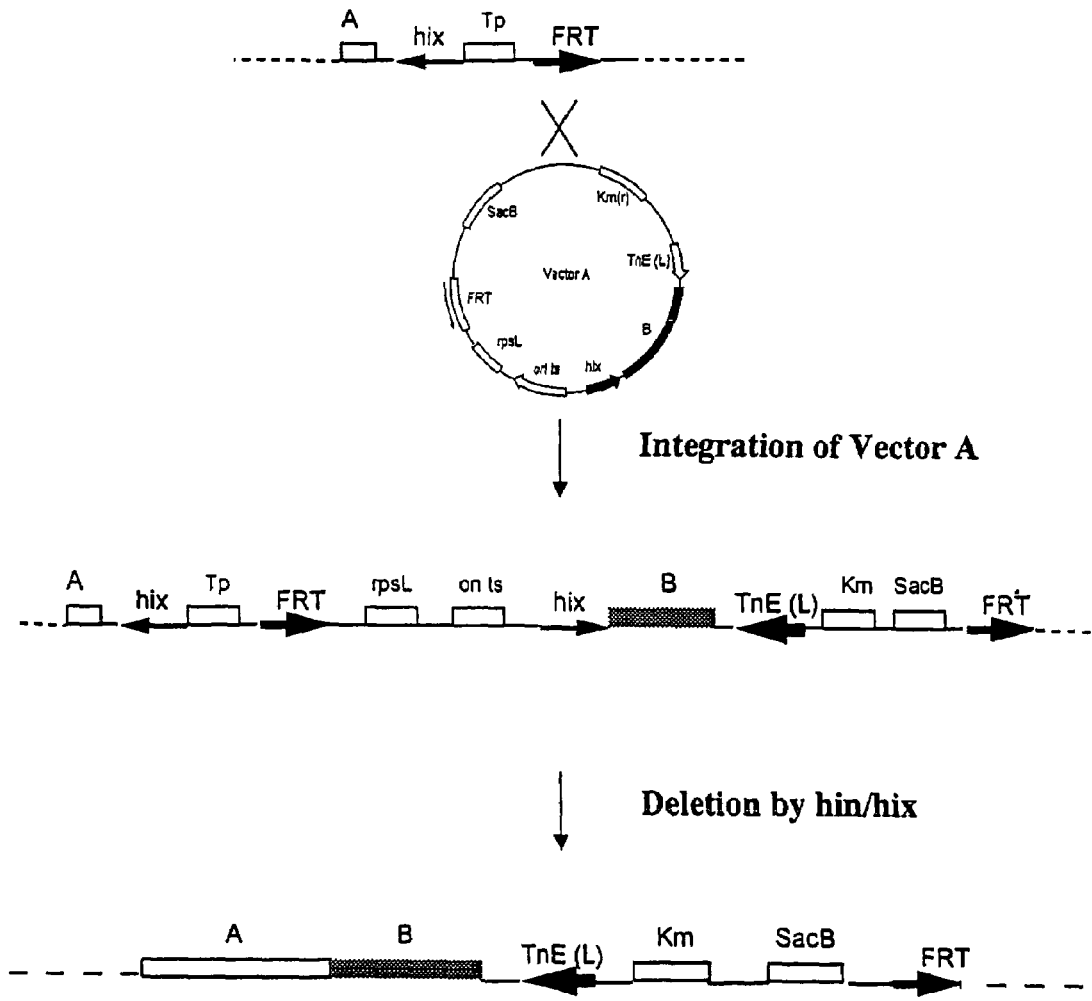
Figure 2B:
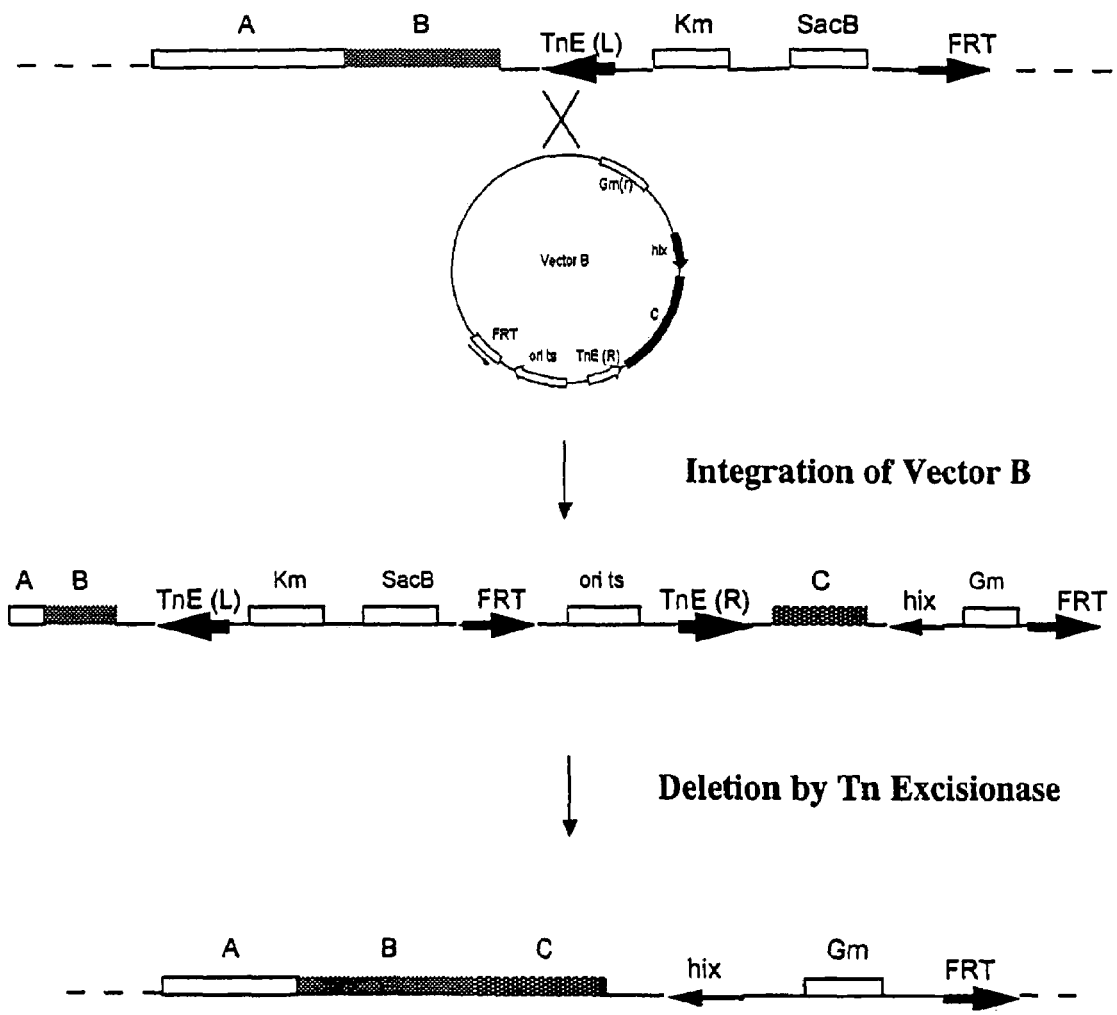

As used herein, all recombinases and excisionases are "site specific" enzymes. "Chromosomal element" is a chromosome or a synthetic chromosome-like element (such as a BAC or YAC). "Replicon" is any nucleic acid that can be maintained by a cell.

Beyond a certain size it becomes difficult to manipulate DNA in vitro and introduce it into cells, so an attractive approach is to assemble the larger segments in an already compacted form inside the cell. This invention is directed to a general method for precise DNA fragment assembly of large constructs using removable carrier DNA elements to bring the desired ends together. The method utilizes two separate recombination enzymes to join DNA fragments attached to the ends of the designed recombination cassette, specifically the systems for site specific recombination to Tn1545 [24, 25] or hix [41, 42]. The required recombinases are engineered to be present in the cell (e.g., on one or more plasmids) and their expression can induced at the appropriate time in the assembly procedure.

The procedure can be preformed in vitro, but the advantage of performing the assembly inside an intact cell is the ease of generating a very large DNA without incurring the risk of shearing the DNA. Nonetheless, smaller fragments (on the order of BAC or YAC size) can successfully be assembled in vitro. When the procedure is performed in vivo, the upper limit on size may be 100, 150, 200, 250, 500, 1,000, 1,500, 2,000 for *Streptococcus*, or *Haemophilus*, 3,000, 5,000 kb for *Salmonella* for *E. coli*, and 10,000 to 30,000 kb for yeast.

The shuttle plasmid for delivery for DNA fragments bears an appropriately oriented recombination site (Tn end or hix site) and an FRT site allowing the plasmid to integrate at the unique chromosomal FRT site [27]. The receiving chromosomal construct for assembling fragments bears the right Tn end (or hix site) adjacent to a FRT site [5]. Assembling of DNA fragments into one segment is performed sequentially in the chromosome. DNA fragments subcloned into the shuttle plasmid between the Tn ends and the hix site are delivered into the chromosome via recombination between the chromosomal and plasmid FRT sites.

The second recombination event is then initiated between active Tn ends (or hix sites) and excises a vector part of the shuttle plasmid leaving the delivered DNA fragment with its adjacent Tn end (or hix site) and one FRT site joined to the previously assembled DNA segment in the chromosome. Thus the DNA segments formerly attached to the end of the "carrier" modules are now joined together in a defined fashion after removal of the intervening functional carrier. The system is designed so successive rounds can be conducted using appropriate vectors, selection and recombinases (either Tn or hix).

EXAMPLE 1

Individual steps of the process have been performed with success in a whole cell *E. coli* K-12 derived strains transformed with plasmids bearing the site specific recombination sites, and some combinations have been successfully performed. However, the whole assembly has not yet been completed. To date, the following steps have been performed: 1) integration of frt containing plasmid into the chromosome using expression of FLP; 2) excision of Tn1545 bounded segment from a construct with Tn1545 int/xis; and 3) excision of hix bounded segment with hin.

The following vectors were employed in the test reactions:

TABLE 1

Vectors, Induction system and Citations

| Vector | Induction System | Citation |
|---|---|---|
| pKH66 | p-tac promoter controlled hin expression on pSC101 on vector | Hughes KT, et al., Phase variation in Salmonella: analysis of Hin recombinase and hix Recombination site interaction in vivo. Genes Dev. 1988 August; 2(8): 937-48. |
| pAT295 | expresses Tn1545 excision enzymes int and xis on pHSG576 vector under lac control | Poyart-Salmeron C, et al. Molecular characterization of two proteins involved in the excision of the conjugative transposon Tn1545: homologies with other site-specific recombinases. EMBO J. 1989 August; 8(8): 2425-33 |
| pCP20 | contains Flp cloned under control of temperature sensitive lambda repressor pR on a temperature senstive plasmid derived from pHSG415 | Cherepanov PP, Wackernagel W. Gene disruption in *Escherichia coli*: TcR and KmR cassettes with the option of Flp-catalyzed excision of the antibiotic-resistance determinant. Gene. 1995 May 26; 158(1): 9-14). |
| pEAW38 | bearing the Flp gene under control of lambda pR and temperature sensitive repressor on pACYC vector. | Huang LC, et al., A bacterial model system for chromosomal targeting. Nucleic Acids Res. 1991 Feb. 11; 19(3): 443-8). |
| pHSG | | Hashimoto-Gotoh T, Franklin FC, Nordheim A, Timmis KN. Specific-purpose plasmid cloning vectors. I. Low copy number, temperature-sensitive, mobilization-defective pSC101-derived containment vectors. Gene. 1981 December; 16(1-3): 227-35. |

All references cited herein are incorporated by reference in their entirety for all purposes.

1. Muyrers, J. P., et al., *Point mutation of bacterial artificial chromosomes by ET recombination*. EMBO Rep, 2000.1 (3): p. 239-43.
2. Martinez-Morales, F., et al., *Chromosomal integration of heterologous DNA in Escherichia coli with precise removal of markers and replicons used during construction*. J Bacteriol, 1999. 181(22): p. 7143-8.
3. Koob, M. D., et al., *Minimizing the genome of Escherichia coli. Motivation and strategy*. Ann N Y Acad Sci, 1994. 745: p. 1-3.
4. Muyrers, J. P., et al., *Rapid modification of bacterial artificial chromosomes by ET-recombination*. Nucleic Acids Res, 1999. 27(6): p. 1555-7.
5. Peredelchuk, M. Y. and G. N. Bennett, *A method for construction of E. coli strains with multiple DNA insertions in the chromosome*. Gene, 1997. 187(2): p. 231-8.
6. Lorbach, E., et al., *Site-specific recombination in human cells catalyzed by phage lambda integrase mutants*. J Mol Biol, 2000. 296(5): p. 1175-81.
7. Cherepanov, P. P. and W. Wackernagel, *Gene disruption in Escherichia coli: TcR and KmR cassettes with the option of Flp-catalyzed excision of the antibiotic-resistance determinant*. Gene, 1995. 158(1): p. 9-14.
8. Chiang, S. L. and J. J. Mekalanos, *Construction of a Vibrio cholerae vaccine candidate using transposon delivery and FLP recombinase-mediated excision*. Infect Immun, 2000. 68(11): p. 6391-7.
9. Posfai, G., et al., *In vivo excision and amplification of large segments of the Escherichia coli genome*. Nucleic Acids Res, 1994. 22(12): p. 2392-8.
10. Buchholz, F., P. O. Angrand, and A. F. Stewart, *Improved properties of FLP recombinase evolved by cycling mutagenesis*. Nat Biotechnol, 1998. 16(7): p. 657-62.
11. Yoon, Y. G., J. H. Cho, and S. C. Kim, *Cre/loxP-mediated excision and amplification of large segments of the Escherichia coli genome*. Genet Anal, 1998. 14(3): p. 89-95.
12. Tsuda, M., *Use of a transposon-encoded site-specific resolution system for construction of large and defined deletion mutations in bacterial chromosome*. Gene, 1998. 207(1): p. 33-41.
13. Dale, E. C. and D. W. Ow, *Gene transfer with subsequent removal of the selection gene from the host genome*. Proc Natl Acad Sci USA, 1991. 88(23): p. 10558-62.
14. Cheng, T. H., et al., *Controlling gene expression in yeast by inducible site-specific recombination*. Nucleic Acids Res, 2000. 28(24): p. E108.
15. Delneri, D., et al., *Exploring redundancy in the yeast genome: an improved strategy for use of the cre-loxP system*. Gene, 2000. 252(1-2): p. 127-35.
16. Palmeros, B., et al., *A family of removable cassettes designed to obtain antibiotic-resistance-free genomic modifications of Escherichia coli and other bacteria*. Gene, 2000. 247(1-2): p. 255-64.
17. Mao, X., Y. Fujiwara, and S. H. Orkin, *Improved reporter strain for monitoring Cre recombinase-mediated DNA excisions in mice*. Proc Natl Acad Sci USA, 1999. 96(9): p. 5037 42.
18. Caparon, M. G. and J. R. Scott, *Excision and insertion of the conjugative transposon Tn916 involves a novel recombination mechanism*. Cell, 1989. 59(6): p. 1027-34.
19. Storrs, M. J., et al., *Conjugative transposition of Tn916 requires the excisive and integrative activities of the transposon-encoded integrase*. J Bacteriol, 1991. 173 (14): p. 4347-52.
20. Scott, J. R., et al., *Conjugative transposition of Tn916: preferred targets and evidence for conjugative transfer of a single strand and for a double-stranded circular intermediate*. Mol Microbiol, 1994. 11(6): p. 1099-108.
21. Manganelli, R., S. Ricci, and G. Pozzi, *Conjugative transposon Tn916: evidence for excision with formation of 5'-protruding termini*. J Bacteriol, 1996. 178(19): p. 5813-6
22. Rudy, C., et al., *Excision of a conjugative transposon in vitro by the Int and X is proteins of Tn916*. Nucleic Acids Res, 1997. 25(20): p. 4061-6.
23. Connolly, K. M., M. Iwahara, and R. T. Clubb, *X is protein binding to the left arm stimulates excision of conjugative transposon Tn916*. J Bacteriol, 2002. 184(8): p. 2088-99.
24. Poyart-Salmeron, C., et al., *The integration-excision system of the conjugative transposon Tn 1545 is structurally and functionally related to those of lambdoid phages*. Mol Microbiol, 1990. 4(9): p. 1513-21.
25. Trieu-Cuot, P., et al., *Sequence requirements for target activity in site-specific recombination mediated by the Int protein of transposon Tn 1545*. Mol Microbiol, 1993. 8(1): p. 179-85.
26. Platt, R., et al., *Genetic system for reversible integration of DNA constructs and lacZ gene fusions into the Escherichia coli chromosome*. Plasmid, 2000. 43(1): p. 12-23.
27. Huang, L. C., E. A. Wood, and M. M. Cox, *A bacterial model system for chromosomal targeting*. Nucleic Acids Res, 1991. 19(3): p. 443-8.

28. Kim, S. Y., et al., *Modification of bacterial artificial chromosome clones using Cre recombinase: introduction of selectable markers for expression in eukaryotic cells.* Genome Res, 1998. 8(4): p. 404-12.
29. Choi, S., et al., *A new approach for the identification and cloning of genes: the pBAC which system using Cre/lox site-specific recombination.* Nucleic Acids Res, 2000. 28(7): p. E19.
30. Golic, M. M., et al., *FLP-mediated DNA mobilization to specific target sites in Drosophila chromosomes.* Nucleic Acids Res, 1997. 25(18): p. 3665-71.
31. Christ, N., T. Corona, and P. Droge, *Site-specific recombination in eukaryotic cells mediated by mutant lambda integrases: implications for synaptic complex formation and the reactivity of episomal DNA segments.* J Mol Biol, 2002. 319(2): p. 305-14.
32. Sclimenti, C. R., B. Thyagarajan, and M. P. Calos, *Directed evolution of a recombinase for improved genomic integration at a native human sequence.* Nucleic Acids Res, 2001. 29(24): p. 5044-51.
33. Sauer, B. and N. Henderson, *Targeted insertion of exogenous DNA into the eukaryotic genome by the Cre recombinase.* New Biol, 1990. 2(5): p. 441-9.
34. Call, L. M., et al., *A cre-lox recombination system for the targeted integration of circular yeast artificial chromosomes into embryonic stem cells.* Hum Mol Genet, 2000. 9(12): p. 1745-51.
35. Feng, Y. Q., et al., *Site-specific chromosomal integration in mammalian cells: highly efficient CRE recombinase-mediated cassette exchange.* J Mol Biol, 1999. 292(4): p. 779-85.
36. Thyagarajan, B., et al., *Mammalian genomes contain active recombinase recognition sites.* Gene, 2000. 244(1-2): p. 47-54.
37. Diaz, V., et al., *The prokaryotic beta-recombinase catalyzes site-specific recombination in mammalian cells.* J Biol Chem, 1999. 274(10): p. 6634-40.
38. Olivares, E. C., R. P. Hollis, and M. P. Calos, *Phage R4 integrase mediates site-specific integration in human cells.* Gene, 2001. 278(1-2): p. 167-76.
39. Johnson, R. C., *Mechanism of site-specific DNA inversion in bacteria.* Curr Opin Genet Dev, 1991. 1(3): p. 404-11.
40. Johnson, R. C., *Bacterial Site-Specific DNA Inversion Systems*, in *Mobile DNA II*, N. L. Craig, Craigie, R., Gellert, M., Lambowitz. A. M., Editor. 2002, ASM Press: Washington, D.C. p. 230-271.
41. Moskowitz, I. P., K. A. Heichman, and R. C. Johnson, *Alignment of recombination sites in Hin-mediated site-specific DNA recombination.* Genes Dev, 1991. 5(9): p. 1635-45.
42. Haykinson, M. J., et al., *The Hin dimer interface is critical for Fis-mediated activation of the catalytic steps of site-specific DNA inversion.* Curr Biol, 1996. 6(2): p. 163-77.
43. Merickel, S. K., M. J. Haykinson, and R. C. Johnson, *Communication between Hin recombinase and Fis regulatory subunits during coordinate activation of Hin-catalyzed site-specific DNA inversion.* Genes Dev, 1998. 12(17): p. 2803-16.
44. Stark, W. M., M. R. Boocock, and D. J. Sherratt, *Site-specific recombination by Tn3 resolvase.* Trends Genet, 1989. 5(9): p. 304-9.
45. Grindley, N. D. F., *The Movement of Tn3-Like Elements: Transposition and Cointegrate Resolution*, in *Mobile DNA II*, N. L. Craig, Craigie, R., Gellert, M., Lambowitz. A. M., Editor. 2002.
46. Arnold, P. H., et al., *Mutants of Tn3 resolvase which do not require accessory binding sites for recombination activity.* Embo J, 1999. 18(5): p. 1407-14.
47. Canosa, I., et al., *Site-specific recombination by the beta protein from the streptococcal plasmid pSM19035: minimal recombination sequences and crossing over site.* Nucleic Acids Res, 1996. 24(14): p. 2712-7.
48. Rojo, F. and J. C. Alonso, *The beta recombinase of plasmid pSM19035 binds to two adjacent sites, making different contacts at each of them.* Nucleic Acids Res, 1995. 23(16): p. 3181-8.
49. Canosa, I., et al., *beta Recombinase catalyzes inversion and resolution between two inversely oriented six sites on a supercoiled DNA substrate and only inversion on relaxed or linear substrates.* J Biol Chem, 1998. 273(22): p. 13886-91.

What is claimed is:

1. A method for the assembly of large DNA fragments, comprising:
   a) manipulating a replicon to comprise in order a final excision site, a first fragment, a first excision site and a first recombinase site;
   b) manipulating a first vector to comprise in order the first recombinase site from step a), undesired vector sequences, the first excision site from step a), a second fragment, and a second excision site;
   c) inserting the first vector into the replicon using a first recombinase so that the two first site specific excision sites are oriented in an appropriate orientation for excision with undesired vector sequences therebetween;
   d) treating the replicon with a first excisionase to completely remove the undesired vector sequences including both first excisionase sites and bring the second fragment directly adjacent to the first fragment;
   e) manipulating a second vector to comprise in order the first recombinase site from step a), undesired vector sequences, the second excision site from step b), a third fragment, and the first excision site from step a);
   f) inserting the second vector into the replicon using the first recombinase so that the two second site specific excision sites are oriented in an appropriate orientation for excision with undesired vector sequences therebetween;
   g) treating the replicon with a second excisionase to completely remove the undesired vector sequences including both second excisionase sites and bring the third fragment directly adjacent to the second fragment;
   h) repeating steps b-g using at least the first and second excisionases to make an assembled DNA, wherein the final vector also comprises the final excision site 5' to all other sequences and in an appropriate orientation for excision; and
   i) excising and circularizing the assembled DNA with a final excisionase.

2. The method of claim 1, which is performed in vivo.

3. The method of claim 1, which is performed in vitro.

4. The method of claim 1, wherein the final excisionase site is lox and the final excisionase is cre, the first recombinase is FRT, the first excisionase site is hix and the first excisionase is hin, the second excisionase site is TNE (L/R) and the second excisionase is Tn excisionase.

5. The method of claim 1, wherein the assembled DNA fragment (exclusive of the original replicon) is greater than 100, 150, 200, 250, 500, 1000, 1500, 2000, 3000, or 5000 kb.

6. A method for the assembly of large DNA fragments in vivo, comprising:
   a) manipulating a replicon to comprise in order a first fragment, a first excision site and a first recombinase site;
   b) manipulating a first vector to comprise in order the first recombinase site from step a), undesired vector sequences, the first excision site from step a), a second fragment, and a second excision site;
   c) inserting the first vector into the replicon in vivo using a first recombinase so that the two first site specific excision sites are oriented in an appropriate orientation for excision with undesired vector sequences therebetween;
   d) treating the replicon with a first excisionase in vivo to completely remove the undesired vector sequences including both first excisionase sites and bring the second fragment directly adjacent to the first fragment;
   e) manipulating a second vector to comprise in order the first recombinase site from step a), undesired vector sequences, the second excision site from step b), a third fragment, and the first excision site from step a);
   f) inserting the second vector into the replicon in vivo using the first recombinase so that the two second site specific excision sites are oriented in an appropriate orientation for excision with undesired vector sequences therebetween;
   g) treating the replicon with a second excisionase in vivo to completely remove the undesired vector sequences including both second excisionase sites and bring the third fragment directly adjacent to the second fragment; and
   h) optionally repeating steps b-g using at least the first and second excisionases in vivo to make an assembled DNA.

7. The method of claim 6, wherein the first recombinase is FRT, the first excisionase site is hix and the first excisionase is hin, the second excisionase site is TNE (L/R) and the second excisionase is Tn excisionase.

8. The method of claim 6, wherein the assembled DNA fragment (exclusive of the original replicon) is greater than 100, 150, 200, 250, 500, 1000, 1500, 2000, 3000, or 5000 kb.

* * * * *